United States Patent [19]

Carty

[11] Patent Number: 5,013,650

[45] Date of Patent: May 7, 1991

[54] INCREASED FERMENTATION YIELD OF EXPRESSED PROTEIN

[75] Inventor: Christine E. Carty, Lansdale, Pa.

[73] Assignee: Merck & Co., Inc., Rahway, N.J.

[21] Appl. No.: 236,704

[22] Filed: Aug. 25, 1988

Related U.S. Application Data

[63] Continuation-in-part of Ser. No. 762,000, Aug. 2, 1985, abandoned.

[51] Int. Cl.$^5$ .............................................. C12N 15/67
[52] U.S. Cl. .................................. 435/69.1; 435/255; 435/256; 935/37
[58] Field of Search ...................... 935/28, 37, 56, 65, 935/69; 435/69.3, 69.4, 69.9, 69.1, 71.1, 255, 256, 940, 942

[56] References Cited

PUBLICATIONS

Fieschko, J., et al., *Biotech. and Bioeng.*, 29, 1113–1121 (1987).
Blanch, H., et al., (editors), *Comprehensive Biotechnology*, vol. 3, Pergamon Press, Oxford, 1985, pp. 442–443.
Stepien et al., Synthesis of a Human Insulin Gene GENE, 24 (1983) 289–297.
Kramer et al., Regulated Expression of a Human Interferon Gene in Yeast: Control by Phosphate Conc. or Temp. P.N.A.S., 81 (Jan. 1984) 367–370.
Miyanohara et al., Expression of Hepatitis B Surface Antigen in Yeast P.N.A.S., 80 (Jan. 1983) 1–5.

*Primary Examiner*—Richard A. Schwartz
*Attorney, Agent, or Firm*—Roy D. Meredith; Charles M. Caruso; Donald J. Perrella

[57] ABSTRACT

A galactose-regulated yeast strain expresses a desired protein in improved yield by growing the transformed yeast cells in culture in fed-batch mode and replacing the culture medium with fresh medium before adding the galactose to induce expression of the foreign protein.

12 Claims, 1 Drawing Sheet

_5,013,650_

INCREASED FERMENTATION YIELD OF EXPRESSED PROTEIN

This is a continuation-in-part of application Ser. No. 762,000, filed Aug. 2, 1985, now abandoned.

BACKGROUND OF THE INVENTION

The use of transformed eucaryotic hosts to express a desired foreign protein is known in the art through the use of recombinant DNA techniques. The transformed cells containing a vector having DNA coding for the desired foreign protein are then grown in cell culture using conventional techniques and the foreign protein, if secreted by the transformed host, is isolated from the cell culture fluids or, if not secreted, is isolated by rupturing the cells.

A modification of the fermentation techniques is to employ a vector which does not produce the desired foreign protein until a specific nutrient is added to the culture medium. Galactose is such a nutrient medium which can be used to induce expression of the desired foreign protein using techniques known to the art (Stepien et al., Gene 24: 289-298, 1983). While the galactose induction system works well to initiate expression of the desired foreign protein in batch mode, it works poorly in fed-batch mode. It would be desirable to obtain the desired protein in higher yield using fed-batch mode.

OBJECTS OF THE INVENTION

It is, accordingly, an object of the present invention to provide a process for obtaining a desired foreign protein in increased yield in a galactose-induced fed-batch fermentation process. This and other objects of the present invention will be apparent from the following description.

SUMMARY OF THE INVENTION

A galactose-regulated yeast strain expresses a desired protein in improved yield by growing the transformed yeast cells in culture in fed-batch mode and replacing the culture medium with fresh medium before adding the galactose to induce expression of the foreign protein.

DETAILED DESCRIPTION

Figure 1:
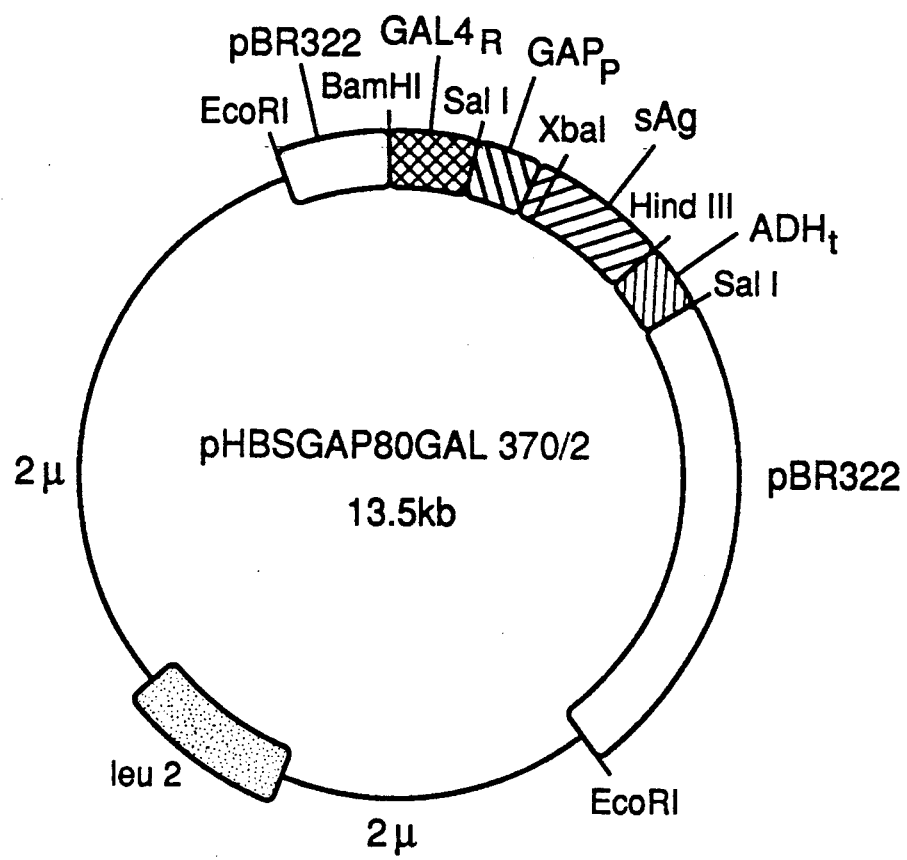
FIG. 1 depicts the restriction map of plasmid pHBSGAP80GAL370/2.

According to the present invention, eucaryotic cells are transformed by insertion of a vector containing DNA constructed to express a desired protein when induced by galactose. The vector also contains DNA coding for the production of an essential nutrient, e g., leucine, uracil, or tryptophan which is not made by non-transformed host cells. This assures that only host cells which retain the recombinant plasmid vector will reproduce as any cells which lose the plasmid will die. The recombinant eucaryotic cells, e.g. *Saccharomyces cerevisiae*, are used to inoculate a leucine and galactose deficient culture medium, e.g., an agar slant.

The host cells are then grown in culture according to techniques suitable for culture of the particular cells chosen to express the desired end product. When the cell density is at or about its maximum and the cells are in late log/early stationary phase, the cells are placed in fresh cell culture medium containing galactose to induce expression. The cells then are incubated for 2 to 3 cell doublings, to assure maximum expression of product. The cells are washed before being placed in fresh cell culture medium. Washing may be done with saline, phosphate buffered saline or other physiologically acceptable solution.

Depending upon the type of host cells and the desired protein, the desired protein may be secreted into the medium in which case a synthetic culture medium is used to facilitate recovery of the desired protein. If the desired protein is not secreted into the medium, it is obtained by rupturing the cells at temperatures of from about 2° to about 8° C. and isolating the desired protein by any suitable means.

While the present invention is exemplified in the following description with reference to a specific yeast strain, it is to be understood that the invention may be practiced equally as well with other yeast strains.

The following examples illustrate the present invention without, however, limiting the same thereto.

EXAMPLE 1

The Gal4 regulatory region between the Gal1 and Gal10 genes of yeast *Saccharomyces cerevisiae* was isolated as a 370 bp XhoI-Sau3A fragment from plasmid pLGSD5, Guarente et al., *Proc. Natl. Acad. Sci.*, USA 79:7410-7414 (1982). This fragment was converted by standard techniques to an −370 bp BamH1-Sal1 fragment and cloned as a BamH1-Sal1 substitution into the yeast expression vector pC1/1, a hybrid plasmid between pBR322 and a two micron circle plasmid joined at their EcoR1 sites, Brake et al., *Proc. Natl. Acad. Sci.*, USA 81:4642-4646 (1984) to give plasmid pC1/1GAL4/370. The −1.6 kb expression cassette containing 376 bp of GAPDH promoter sequence, Holland et al., *J. Biol. Chem.* 254: 9839-9845 (1979) and Travis et al., *J. Biol. Chem.* 260:4384-4389 (1985), the sequence for the entire coding region of the mature hepatitis B surface antigen and 128 bp of 3' untranslated sequence, Valenzuela et al., in Fields, Jaenisch and Fox (eds.), *Animal Virus Genetics*, Academic Press, New York, 1980, as well as the 350 bp ADH1 terminator, Bennetzen et al., *J. Biol. Chem.* 257:3018-3025, (1982), was constructed as a SalI fragment and cloned into the SalI site of pC1/1GAL4/370. A plasmid, pHBSGAP8-0GAL370/2 was obtained which had the expression cassette in the desired orientation relative to the GAL regulatory region.

Yeast strain 2150-2-3 (Mata, leu2, ade1, nib6+, [cir°], derived from a genetic cross between strain Y379-5-D cyh2 nib1 (rho−), Livingston, *Genetics* 86:73 (1977), and DC O4 a *Ade*1, Adex, leu2-04 (cir°), Broach, *Cell* 21:501 (1980), was transformed with pHBSGAP80GAL370/2 essentially according to Hinnen et al., *Proc. Natl. Acad. Sci.*, USA 75: 1919-1933 (1978), to give tranformed yeast strain p5. Leu+ transformants were selected and maintained in synthetic complete medium lacking leucine (SC-leu). SC-leu medium contained 0.67% yeast nitrogen base without amino acids; 1% succinic acid; 0.6% NaOH; 2% glucose; 100 μg/ml adenine; 30 μg/ml each of uridine, tyrosine and lysine; 20 μg/ml each of tryptophan, histidine, arginine and methionine; and 200 μg/ml of threonine.

EXAMPLE 2

A. A leucine and galactose deficient agar slant was inoculated with 1 ml of reconstituted lyophilized recombinant *Saccharomyces cerevisiae* cells, strain P5, which expresses the HBsAg gene when induced with galactose. After 4 days at 28° C. the slant was resuspended in 5 ml yeast extract-peptone-dextrose (YEPD) medium and a 250 ml flask containing 46 ml of uninoculated YEPD medium was inoculated with 4 ml of the cell suspension The flask was incubated at 28° C. in a shaker/incubator at 350 rpm for 7.5 hours. The contents of the 250 ml flask were transferred to a two liter flask containing 450 ml of uninoculated YEPD medium and the incubation was continued for 19 hours.

This 500 ml yeast culture (O.D. of 7.5 at 660 nm) was added to a 16 L New Brunswick fermenter containing 5.0 L of uninoculated YEPD medium. The fermentation was continued at 28° C., stirred initially at 300 rpm and sparged with air at a rate of 3 L/minute. Throughout the fermentation dissolved oxygen was controlled at approximately 10% of saturation and the pH at 5.0. After cell growth began to increase, YEPD medium was pumped into the fermenter from the 18th to the 52nd hour of the fermentation at the following rates:

| Hours | Rates (ml/hour) |
|---|---|
| 18–27 | 60 |
| 27–29.5 | 130 |
| 29.5–52 | 180 |

At hour 52 cell density was at a maximum and the cells were in late log/early stationary phase.

B. Approximately 1.0 L of yeast culture was removed at 52 hours. Half of the cell broth (500 ml) was transferred to a 2 L flask; galactose was added to a final concentration of 2% (w/v). The flask was incubated at 28° C. in a shaker/incubator at 350 rpm for 20 hours.

Cell growth of the culture was estimated by determination of O.D. at 660 nm and by measurement of dry weight. The O.D. was 36 and the dry weight was 34.2 g/L. The cells were then ruptured at 4° C. by shearing with glass beads. The HBsAg concentration was less than 0.0001 mg/L by AUSRIA.

C. The other 500 ml of fermenter culture was centrifuged at 10,000×g for 20 minutes. The pelleted cells were resuspended in 400 ml phosphate buffered saline (PBS) and centrifuged again at 10,000×g for 20 minutes to remove entrained medium components. The pelleted cells were resuspended again in 400 ml of PBS and centrifuged a third time at 10,000×g for 20 minutes. The pelleted yeast cells were then resuspended in 500 ml yeast extract-peptone, galactose was added to a final concentration of 2% (w/v) and the culture was incubated at 28° C. in a shaker/incubator at 350 rpm for 20 hours.

Cell growth of the culture was estimated by determination of O.D. at 660 nm and by measurement of dry weight. The O.D. was 44 and the dry weight was 35.1 g/L. The cells were then ruptured at 4° C. by shearing with glass beads. The HBsAg concentration was 0.15 mg/L by AUSRIA.

The failure of the culture in Step B to express meaningful levels of HBsAg was not due to glucose suppression. Glucose concentrations were determined at intervals throughout the course of this experiment by means of a Beckman Glucose Analyzer II. Under the conditions employed, this instrument was capable of determining glucose concentrations as low as 0.1 g/liter. Analyses were also conducted for HBsAg particles using the AUSRIA assay.

The glucose and HBsAg concentrations set forth in Table I were obtained for the time indicated.

TABLE I

| Time (hour) | Glucose (g/L) | HBsAg (mg/ml) |
|---|---|---|
| 3 | 31 | — |
| 17 | 2.5 | 0 |
| 37 | 2.0 | 0 |
| 49 | 0.3 | — |
| 52 | 0.2 | 0 |
| 52.5[1] | <0.1 | — |
| 53 | <0.1 | 0 |
| 69[2] | <0.1 | 0.02 |
| 69[3] | <0.1 | 15 |

[1] galactose added
[2] Step B. unwashed
[3] Step C. washed

EXAMPLE 3

The procedure of part A of Example 1 is repeated. One liter of the yeast culture is then removed and filtered using a 0.45 filter. The yeast cells are then resuspended in 1.0 L yeast extract peptone and galactose is added to a final concentration of 2% (w/v). The culture is then incubated at 28° C. in a shaker/incubator at 350 rpm for 20 hours. HBsAg is obtained in concentration similar to that of Example 1.

EXAMPLE 4

The procedure of part A of Example 1 is repeated. One liter of the yeast culture is then removed and diafiltered against PBS. The yeast cells are then resuspended in 1.0 L yeast extract peptone and galactose is added to a final concentration of 2% (w/v). The culture is then incubated at 28° C. in a shaker/incubator at 350 rpm for 20 hours. HBsAg is obtained in concentration similar to that of Example 1.

What is claimed is:

1. A process for increasing the yield of a foreign protein that is produced under control of a galactose inducible promoter by transformed yeast cells that express the foreign protein when induced with galactose comprising growing the transformed yeast cells in fed-batch mode using a medium substantially free of galactose until the cell density is at or about its maximum, and removing at least some of the spent culture medium from the yeast cells by washing the cells in a physiologically acceptable medium before continuing the incubation of the transformed yeast in the presence of at least some fresh culture medium and galactose to produce the foreign protein.

2. A process according to claim 1 wherein the spent medium is removed by centrifugation.

3. A process according to claim 1 wherein the spent medium is removed by filtration.

4. A process according to claim 1 wherein the spent medium is removed by diafiltration.

5. A process according to claim 1 wherein substantially all of the culture medium is removed from the yeast cells before continuing the incubation of the transformed yeast in the presence of fresh culture medium and galactose to produce the foreign protein.

6. A process according to claim 5 wherein the spent medium is removed by centrifugation.

7. A process according to claim 5 wherein the spent medium is removed by ultrafiltration.

8. A process according to claim 5 wherein the spent medium is removed by diafiltration.

9. In a method for inducing expression of a foreign protein that is produced under control of a galactose inducible promoter in a transformed yeast by adding galactose to the incubation broth in which the transformed yeast is growing when the cell density is at or about its maximum, the improvement comprising removing at least some of the growth medium by washing the cells with a physiologically acceptable medium and adding the washed cells to fresh medium containing galactose.

10. A process according to claim 1 wherein the physiologically acceptable medium is saline or PBS.

11. A process according to claim 10 wherein the physiologically acceptable medium is saline.

12. A process according to claim 10 wherein the physiologically acceptable medium is PBS.

* * * * *